(12) United States Patent
Turecek et al.

(10) Patent No.: US 6,270,672 B1
(45) Date of Patent: Aug. 7, 2001

(54) DEVICES AND METHODS FOR REMOVING PATHOGENS FROM BIOLOGICAL FLUIDS

(75) Inventors: Peter Turecek, Klosterneuburg; Erwin Mattes, Perchtoldsdorf; Hans Peter Schwarz, Vienna, all of (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/369,692

(22) Filed: Aug. 6, 1999

(51) Int. Cl.[7] .................................................. B01D 61/14
(52) U.S. Cl. .......................... 210/645; 210/651; 210/652; 204/522; 204/527; 204/535; 204/276; 435/173.1
(58) Field of Search ..................... 210/645, 651, 210/652; 204/450, 527, 516, 535, 522, 276; 435/173.1, 173.3

(56) References Cited

U.S. PATENT DOCUMENTS

| | | |
|---|---|---|
| 4,110,175 * | 8/1978 | Ahlgren et al. . |
| 4,322,275 * | 3/1982 | Jain . |
| 4,678,553 * | 7/1987 | Mandle et al. . |
| 5,731,164 * | 3/1998 | Becker et al. . |
| 5,954,937 * | 9/1999 | Farmer . |

FOREIGN PATENT DOCUMENTS

| | | |
|---|---|---|
| 0 050 061 | 9/1981 | (EP) . |
| 0 131 740 | 6/1984 | (EP) . |

OTHER PUBLICATIONS

Eibl, J. et al., "Nanofiltration of Immunoglobulin with 35–nm Filters Fails to Remove Substantial Amounts of HCV", *Biologicals* 24:285–287 (1996).
DiLeo, A.J., "Size Exclusion Removal of Model Mammalian Viruses Using a Unique Membrane System, Part I: Membrane Qualification" *Biologicals* 21:275–286 (1993).
DiLeo, A.J., "Size Exclusion Removal of Model Mammalian Viruses Using a Unique Membrane System, Part II: Module Qualification and Process Simulation" *Biologicals* 21:287–296 (1993).
Manabe, S.I., "Removal of Virus Through Novel Membrane Filtration Method" *Dev. Biol. Stand.* 88:81–90 (1996).
Neuhoff, V. et al., "Improved Staining of Proteins in Polyacrylamide Gels Including Isoelectric Focusing Gels with Clear Background at Nanogram Sensitivity Using Coomassie Brilliant Blue G–250 and R–250" *Electrophoresis* 9:255–262 (1988).
Nishizawa T. et al., "A Novel DNA Virus (TTV) Associated with Elevated Transaminase Levels in Posttransfusion Hepatitis of Unknown Etiology" *Biochem. & Biophy. Res. Comm.* 241:92–97 (1997).
O'Grady, J. et al., "Virus Removal Studies Using Nanofiltration Membranes" *Dev. Biol. Stand.* 88:319–326 (1996).

* cited by examiner

*Primary Examiner*—Ana Fortuna
(74) *Attorney, Agent, or Firm*—Oppenheimer Wolff & Donnelly LLP

(57) ABSTRACT

A method for removing pathogens from biological liquids and an apparatus for performing such a method, said method comprising the steps of providing a biological liquid, wherein pathogens are potentially present, in an apparatus comprising an anode and a kathode and a separation means suitable for separating said pathogens from said pharmaceutically active molecule, said separation means being positioned between said anode and said kathode, applying current between said anode and said kathode, thereby causing one of said pathogens or said pharmaceutically active molecule to pass said separation means and recovering said pharmaceutically active molecule in a form being free of said pathogens as well as an apparatus carrying out the present method.

20 Claims, 5 Drawing Sheets

FILTRATION CHAMBER

FIG. 1

- ⊙ Active Compound
- ☐ Virus

DEVICES AND METHODS FOR REMOVING PATHOGENS FROM BIOLOGICAL FLUIDS

The invention relates to a method for removing pathogens from biological liquids and an apparatus for performing such a method.

The risk of transmission of viruses by blood products is known. There is comprehensive literature available dealing with the inactivation of infectious agents by various methods. These methods include the treatment of biological and pharmaceutical products with chemical substances (e.g. with detergents, solvents etc. or combinations thereof (EP 0 050 061 A, EP 0 131 740 A)), heating steps (e.g. heating in an aqueous solution in the presence of stabilizing agents, heating in the dry state and heating in the solid wet state) and physical methods (e.g. photoinactivation or nanofiltration).

Especially nanofiltration is a very promising technique due to its efficacy especially for industrial production methods.

However, there are several problems connected with nanofiltration: First, due to the small pore sizes it is often difficult to filter biological liquids through a nanofilter. Therefore, biological liquids frequently have to be diluted before and concentrated again after a nanofiltration.

Moreover, nanofilters have varying performance abilities (due to the method of production). Generally nanofilters are no absolute filters, i.e. their cut-off value is not absolute and an unwanted passage of (small) viruses through the filters frequently occurs (see, for example Eibl et al, Biologicals 24(3), 285–287 (1996), Manabe Dev. Biol. Stand. 88, 81–90 (1996) or O'Grady et al., Dev. Biol. Stand 88, 319–326 (1996)).

In order to accelerate the nanofiltration step, especially on a large scale, pressure is applied to facilitate the passage of biological solutions through the filter. Such a pressurizing, however is connected with a risk of breaking of the filter and may enhance a passage of viruses through the filters. Alternatively, if ultrafiltration means are used, an enhanced overflow rate is applied to facilitate membrane passage of proteins contained in the biological liquid (see, for example Di Leo et al., Biologicals 21(3), 287–296 (1993) and Di Leo et al., Biologicals 21(3), 275–286 (1993)).

Due to the sheer forces caused by these additional measures in the filtration steps, viruses or virus components may change their size which allow the passage of the filtration membranes despite the cut-off range which theoretically would not allow a virus passage. Such sheer forces, however, lead to detection of viruses in the filtrate due to change the shape of the virus particles during membrane passage.

It is an object of the present invention to provide an improved method for removing pathogens from biological liquids, especially proteinaceous solutions, with separation means.

It is a further object of the invention to provide a nanofiltration method which is more reliable especially with respect to the definiteness of virus cut-off than the nanofiltration techniques of the prior art. Furthermore, a nanofiltration method suitable for the production of biological products on large scale shall be provided with allows virus reduction without significant loss of protein yield in an industrially applicable method.

These objects are solved by a method for removing pathogens from biological liquids, said biological liquids containing at least one pharmaceutically active molecule, said method comprising the steps of providing a biological liquid, wherein pathogens are potentially present, in an apparatus comprising an anode and a kathode and a separation means suitable for separating said pathogens from said pharmaceutically active molecule, said separation means being positioned between said anode and said kathode, applying current between said anode and said kathode, thereby causing one of said pathogens or said pharmaceutically active molecule to pass said separation means and recovering said pharmaceutically active molecule in a form being essentially free of said pathogens.

Essentially free has to be understood in that more than 99% of the contaminants present in the starting material are removed. Preferred that more than 99,9% and most preferred that more than 99,99% of the pathogens present in the starting material are removed.

The method according to the present invention allows a safe and relieable method for removing pathogens from biological liquids, thereby preventing the necessity of pressure or fast overflow. Moreover, due to the application of electric current it is possible to remove the pathogens from the pharmaceutically active substance not only based on size but also based on relative charge differences.

Biological liquids are liquids that are obtained from biological sources, for instance body liquids such as blood or liquids derived from cell culturing, especially culturing of recombinant cells. All such biological liquids have a certain risk of being contaminated with infectious agents, especially viruses, which should not be present in the final product containing the pharmaceutically active compound.

Such a risk of transmission of viruses is especially given and described for blood products. Under blood products, products of human and animal blood or plasma are understood which are intended for therapeutic, prophylactic or diagnostic applications. Such products may contain proteins, such as enzymes, proenzymes, coagulation factors, enzyme inhibitors, immunoglobulins, albumin, plasminogen, fibrinogen and fibronectin.

The separation means to be used according to the present invention can be any means suitable for separating the viral pathogen from the pharmaceutically active molecule, especially filtration means. According to the present invention a nanofilter preventing viruses from passing through the filter is preferred, for example Millipore PTMK 300 kD Polysulfor, Planova (Asahi) or Viresolve. Such filter means should have a cut-off range of a defined value as applied in current nanofiltration methods. The filter devides the apparatus used for performing the present invention (the filtration chamber) into two compartments. Usually in the first compartment the biological liquid (potentially infected with viral pathogens) is provided, the second compartment may be filled with a suitable puffer.

It is further preferred to use ultrafiltration membranes as a filtration means.

The term pathogen shall for the present invention not only include viruses but also other pathogens with a size comparable to viruses, such as prion pathogens, such as the BSE pathogen or the scrapie pathogen.

Especially for viral contaminations which have a peculiar structure or are very difficult to inactivate by other methods of virus inactivation or virus depletion the present method is very effective.

The method according to the present invention may be performed in a variety of modes depending on the structure and charge of the pathogen relative to the pharmaceutically active molecule. If for example the pathogen is uncharged, it retains in the compartment where it has been introduced due to its lack of electrophoretic mobility. A charged pharmaceutically active molecule, such as a macromolecule, especially a protein, is affected by the applied current and is forced to pass the filtration membrane. It is of course evident that the positioning of the kathode and anode has to be adapted to the biological liquid and to the system of pathogen/pharmaceutically active substance in order to allow an effective separation. This, however, is routine work for the skilled man in the art. The filtration membrane which may be in principle an ultrafilter prevents that the (uncharged) pathogen passes the filter by diffusion.

If the pharmaceutically active substance and the pathogen are equally charged and both have an electrophoretical mobility into the same direction, a filter with a suitable cut-off between the size of the pathogen and the size of the pharmaceutically active molecule prevents the passage of the larger of the two (in most cases: the viral pathogen) from passaging the membrane. Since the sheer forces present in the system according to the present invention are relatively low, a deformation of e.g. pathogen aggregates is unlikely to secure. Moreover, the filtration rate may be controlled by the strength of the electric current, so that a quantitative separation of pharmaceutically active substance and pathogen is achieved. Also the pH of solutions changes the charge particles and pharmaceutically active substances.

If the pathogen and the pharmaceutically active molecule have opposite charges, pathogen and active molecule move to opposite electrodes and an effective separation is made possible by both, the difference in charge and by the separation means if the electric field is maintained.

Virus net charges can vary over the entire pH-spectrum (i.e. 2–10).

The pharmaceutically active molecule to be separated from pathogens with the method according to the present invention is preferably a protein, especially a blood protein. The present method is especially suitable for the blood proteins mentioned above. Proteins are charged molecules and may be forced by an electric field to migrate through the separation means to the positive electrode (anode), whereas pathogens, especially uncharged pathogens, are prevented from passing the filter by the cut-off range of the filter and by their lack of mobility in the electric field.

It is preferred that the protein to be purified according to the present invention from the pathogen is smaller than the pathogens to be separated from the solution so that a filtration means may be used with a cut-off value between the size of the protein and the size of the pathogen.

It is also possible to provide a series of filters with different separation, especially filtration characteristics, e.g. with reducing cut-off sizes, which would allow the separation of e.g. proteins into different molecular weight fractions. Such a method would also allow the separation of components of different sizes from mixtures of active components in addition to the removal of pathogens. This is of specific advantage in the processing of complex biological liquids with a variety of pharmaceutically active molecules of different size and different charge, such as blood plasma or complex cell supernatants.

A further variant of the method according to the present invention consists of providing dialysis membranes with immobilized ampholytes as separation means. Such membranes could easily be designed to exhibit definite isoelectric points due to the composition of ampholyte. Ampholytes are substances or molecules with defined negative or positive charges resulting in a defined isoelectric point.

For such a series of filters a series of compartments is defined in the apparatus for performing the method according to the present invention which compartments may e.g. represent isoelectric areas in the compartments if dialysis membranes with immobilized ampholytes are used. The pharmaceutically active molecule would be trapped in the compartment which relates to its isoelectric point.

The electrofiltration technique according to the present invention therefore does not only allow a separation of pathogens from pharmaceutically active molecules but also a quantitative separation of pharmaceutically active molecules and aggregates or monomers of prion proteins which are proteins with a molecular mass of about 30 kD. Prions are assumed to cause scrapie and scrapie-related diseases which have also been described as transmissible spongiform encephalopathies (TSE) such as scrapie, bovine TSE (BSE), kuru, Creutzfeld Jakob Disease (CJD), Gerstmann-Stra äussler syndrom (GSS) and fatal familiar insomnia (FFI).

Moreover, the present system allows an efficient partition of nucleic acid and proteins, especially with a selection of a suitable puffer system due to the significant difference in charge between nucleic acids and proteins. It also allows the separation of nucleic acid or viral contaminations from suspension of blood cells.

The present method is especially suited to remove viral pathogens, such as hepatitis viruses, HI viruses, Parvoviruses and prion pathogens, especially HAV, HBV, HCV, HGV, HEV, HDV, CMV, HIV-1, HIV-2, Parvovirus B19 and TT-Virus, a recently isolated virus (Nishizawa et al., Biochem. Biophys. Res. Commun. 241, 92–97 (1997)) from biological liquids during the process of preparing a pharmaceutically active molecule from the biological liquid.

In a preferred embodiment of the present invention a filter means is provided with a cut-off value which allows a separation between the pharmaceutically active molecule and aggregates of said molecule. This filter means may be suited also for the separation of pathogens or provided as a second filtration means in the apparatus.

A further separation problem connected with inactivation of viral pathogens may be solved with the method according to the present invention. If a biological liquid containing a pharmaceutically active molecule is treated for viral inactivation by using a chemical substance, it is in most cases important to separate this chemical substance from the pharmaceutically active molecule after the chemical inactivation step together with the inactivated viral pathogens. This is especially a problem in the "solvent/detergent treatment" (see for example EP 0 131 740A), wherein an organic solvent and optionally detergents are used for viral inactivation. Since such a solvent (especially TNBP which is commonly used) may be toxic, such virus inactivating agents have to be separated quantitatively from the pharmaceutical preparation. However, especially potential toxic components which have a binding capacity to proteins, such as TNBP, are difficult to separate from the proteins. In the prior art chromatographic techniques or ultrafiltration systems have been used for this purpose. These methods, however, exhibit a risk that traces of the inactivating agent remains in the protein solution. With the method according to the present invention such substances may easily be separated from the pharmaceutically active molecule by the electrophoretic properties as well as by separation means. Therefore, the method according to the present invention is preferably applied after a virus inactivation step using chemical substances as virucidal agents. This inactivation step may also be performed in the electrophoration apparatus.

Preferably TNBP may be applied with a detergent such as cholate, Triton X-100 or Tween 80. Especially in the case of cholate also the detergent component is a protonable or deprotonable molecule which is—as well as TNBP—easily separatable from the pharmaceutically active molecule, especially if it is a protein. If a heating step should be applied for viral inactivation such a heating step may preferably be performed before or during the method according to the present invention.

Preferably a virus inactivation step is carried out before the current is applied. Such a virus inactivation step may preferably be selected from the group consisting of solvent/ detergent treatment, detergent treatment, pH lowering and chemical treatment.

According to a further aspect the present invention also comprises an apparatus for removing pathogens from biological liquids, said biological liquids containing at least one pharmaceutically active molecule, said apparatus comprising a container for uptake of said biological liquid, an anode, a kathode and a separation means suitable for separating said pathogens from said pharmaceutically active molecules, said separation means being positioned between said anode and said kathode and a current supply and means for applying said current between said anode and said kathode.

Such an apparatus is specifically designed for the method of the present invention and may easily be adapted for the preferred embodiments of the present methods by the man skilled in the art.

E.g. if a heating step shall take place in the apparatus, heating means and temperature controlling means should be provided in the apparatus.

The invention will be explained in more detail by way of the following examples and the drawing figures, yet is not restricted to these particular embodiments.

Figure 1:
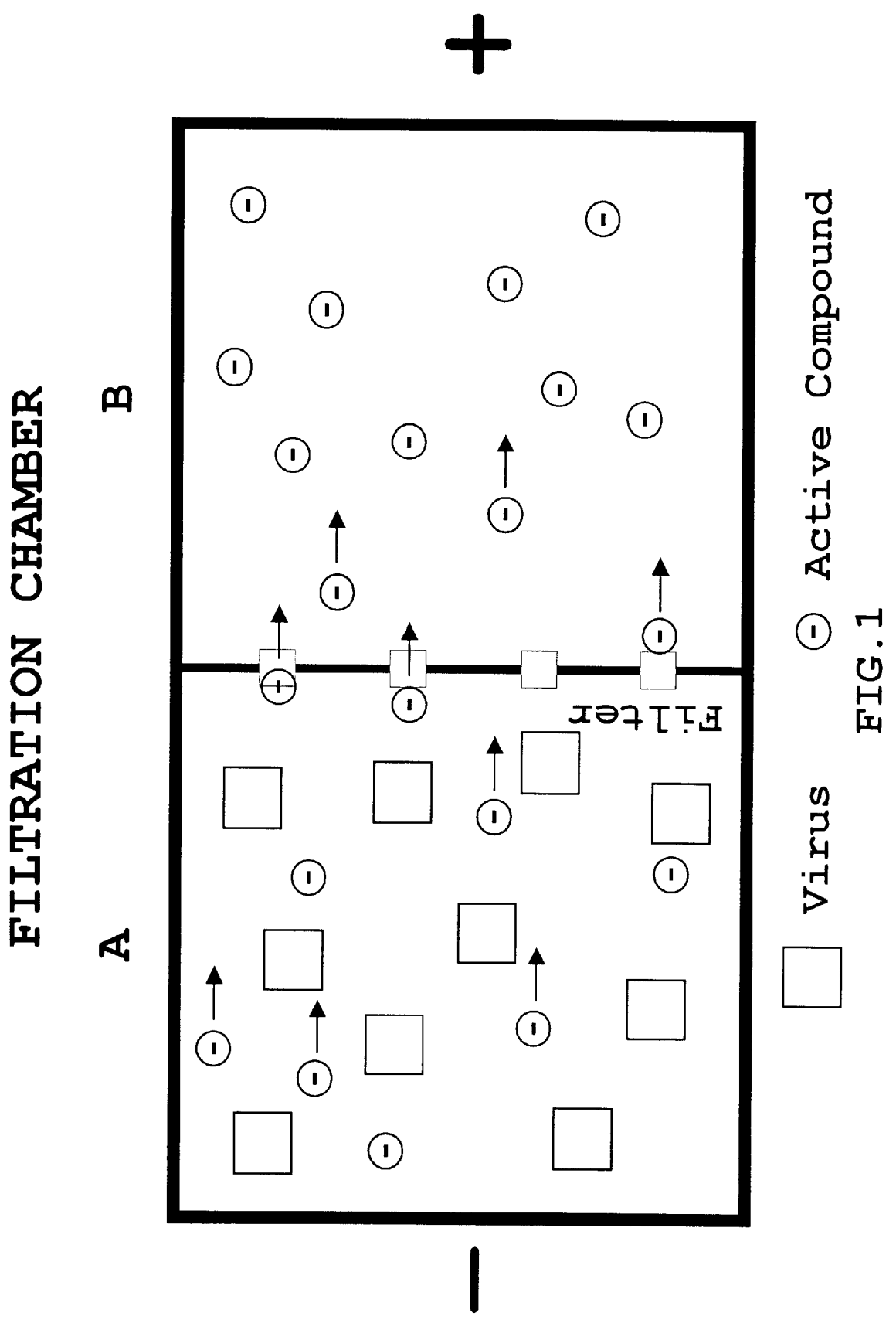

FIG. 1 shows the graphic representation of an embodiment of the present invention wherein a negatively charged pharmaceutically active molecule is separated from a biological solution containing viruses.

EXAMPLES

Figure 2:
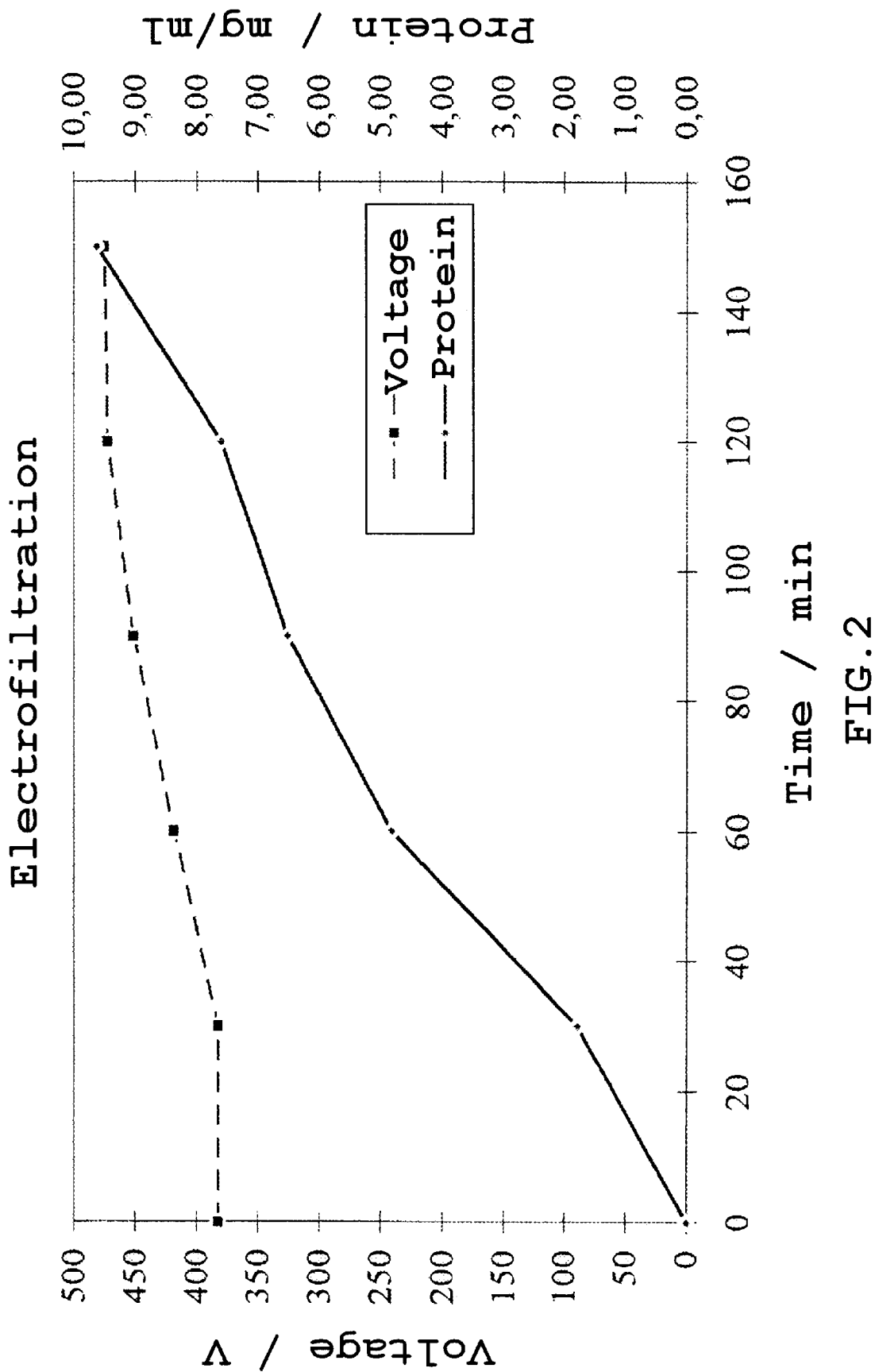
FIG. 2 is a graphical representation of the results of an electrofiltration experiment using plasma cryosupernatant with Parvovirus B19.

The electrofiltration was carried out in a Biotrap BT 1000 (Schleicher & Schuell Inc., Keene, N.H. USA). As stop membranes to the electrode puffer chambers BT 1 membranes (derivatised cellulose; cut-off value 5 kD) have been applied. As separation membrane between the larger starting chamber and smaller filtrate chamber a BT2 membrane (Millipore PTMK 300 kD polysulfone) was used. A puffer containing 10 mM Tris-HCl pH 8.5 was filled into the electrode puffer chambers. The filtrate chamber contained 0.9% sodium chloride solution, the starting chamber contained plasma cryosupernatant with 0.001 volumes of high titer Parvo B19 plasma diluted with 9 volumes 10 mM Tris-HCl puffer pH 8.5. The electrophoretic separation through the filter membrane was performed 2.5 hours under the conditions of the following table 1.

TABLE 1

| time [min] | voltage [V] | current [mA] | power [W] | in the filtrate chamber | | |
|---|---|---|---|---|---|---|
| | | | | protein [mg/ml] | ParvoB19 [GE/ml] | in percent |
| 0 | 382 | 25.0 | 10 | 0.00 | 0.0 E + 0 | 0.00% |
| 30 | 382 | 25.0 | 10 | 1.78 | 2.9 E + 3 | 0.02% |
| 60 | 418 | 25.0 | 10 | 4.82 | 1.4 E + 3 | 0.01% |
| 90 | 451 | 25.0 | 10 | 6.51 | 4.1 E + 3 | 0.03% |
| 120 | 472 | 25.0 | 12 | 7.59 | 1.4 E + 4 | 0.11% |
| 150 | 475 | 25.0 | 12 | 9.62 | 1.5 E + 4 | 0.12% |
| starting material | | | | 6.30 | 1.3 E + 7 | 100.00% |

The protein content of the solution in the filtrate chamber was determined by the standard method of the BCA protein assay (Pierce, Rockford, Ill., USA) with precinorm protein control serum (Boehringer Mannheim, Mannheim, Germay) as standard.

Parvo B19 content was determined with PCR (polymerase chain reaction) according to the following method: To the respective samples a defined copy number of an internal standard was added before the extraction. The internal standard had the same recognition sites for primers as the specific targeting sequence on the B19 DNA but had a difference in length. Samples were extracted and 10 μl aliquots of the extracts were used for the PCR. PCR solution had a total volume of 50 μl and contained 1 U AmpliTaq Gold$^{TMi}$ (Perkin Elmer, Norwalk, Conn., USA), 5 μl 10×puffer with $MgCl_2$ (Perin Elmer), 200 μM dNTPs and 30 pmol of primers KK5 (5'-GCC AAG AAA CCC CGC ATT ACC-3') and KK6 (5'-ACC AGT TTA CCA TAG TTT GAA-3'). Samples were incubated for 10 min at 95° C. and afterwards 36 cycles of amplification were performed according to the following scheme: 15 sec at 95° C., 30 sec at 58° C. and 30 sec at 72° C. Finally, incubation for 10 min at 72° C. was performed. The amplified samples were electrophoretically separated and genome equivalents (GE) of Parvo B19 was determined by comparison of the intensity of Parvo B19 signal with the intensity of the signal of the internal standard.

In order to characterize the partition of proteins the samples were subjected to a reduced SDS polyacrylamide gelelectrophoresis with pre-manufactured ExcelGel gradient gels (8%–18%, Pharmacia, Uppsala, Sweden) on a horizontal flat bed apparatus accordingly to the manufactures instructions. The gel was stained with Coomassie Brilliant Blue G-250 (BioRad, Hercules, Calif., USA) accordingly to the colloid method (Neuhoff et al.: Electrophoresis 9 (1988), 255–262) and dried afterwards. The gel is depicted in FIG. 3.

Figure 3:
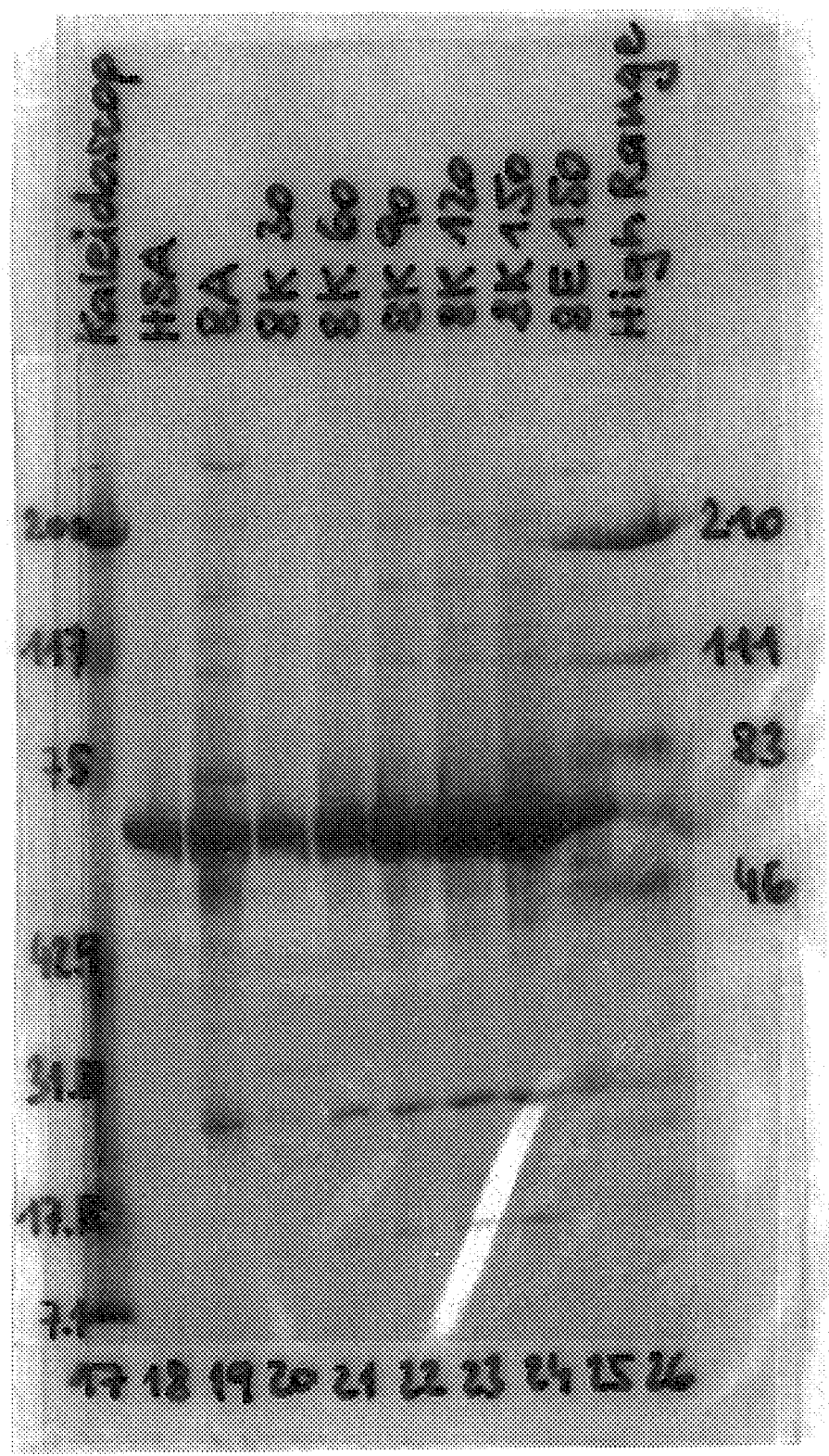
FIG. 3 shows the SDS PAGE for this experiment.

From table 1 and FIG. 3 it is evident that also the small Parvo B19 virus may be efficiently separated by electrofiltration from the proteins of the cryosupernatant which is a very complex biological liquid with a large number of classes of pharmaceutically active molecules. In total only 0.12% of the genom equivalent of Parvo virus B19 is detectable in the filtrate chamber indicating a virus reduction of around $10^{-3}$. The pattern of the reduced SDS polyacrylamid gel clearly shows that proteins which are smaller than 210 kD pass the membrane with 300 kD cut-off limit. A protein band which is larger than 210 kD (see lanes 8A (starting material) and 8E150 (contents of starting chamber after 150 min current applied), however, is retained by the membrane and is not detectable in the samples of the filtrate chambers (see lanes 8K30 to 8K150 (contents of filtrate chamber after 30 to 150 min current applied)). This clearly shows that the cut-off range of the membrane is effective.

Preferred apparatus

Figure 4:
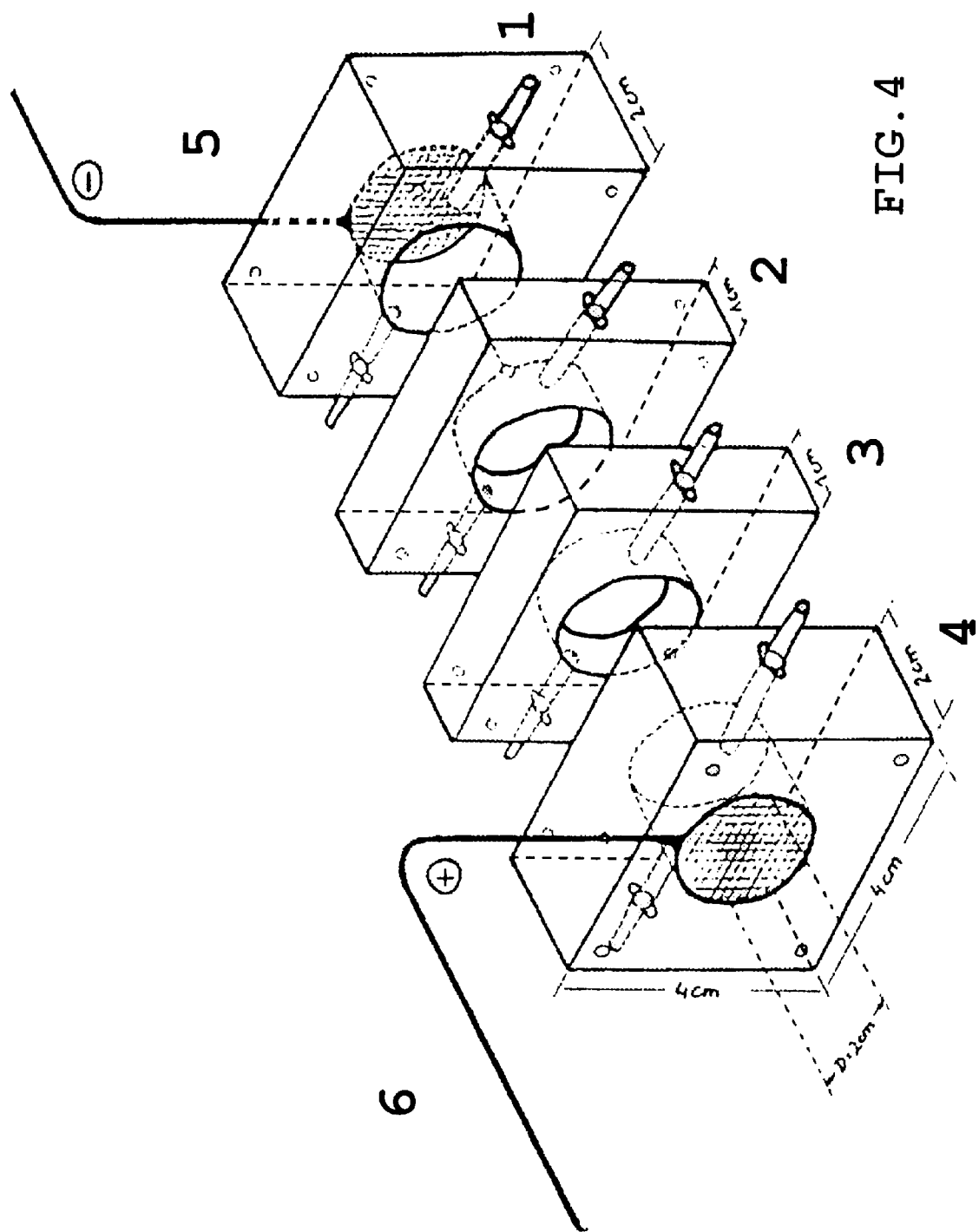
FIGS. 4 and 5 show a preferred apparatus for carrying out the present invention.
Figure 5:
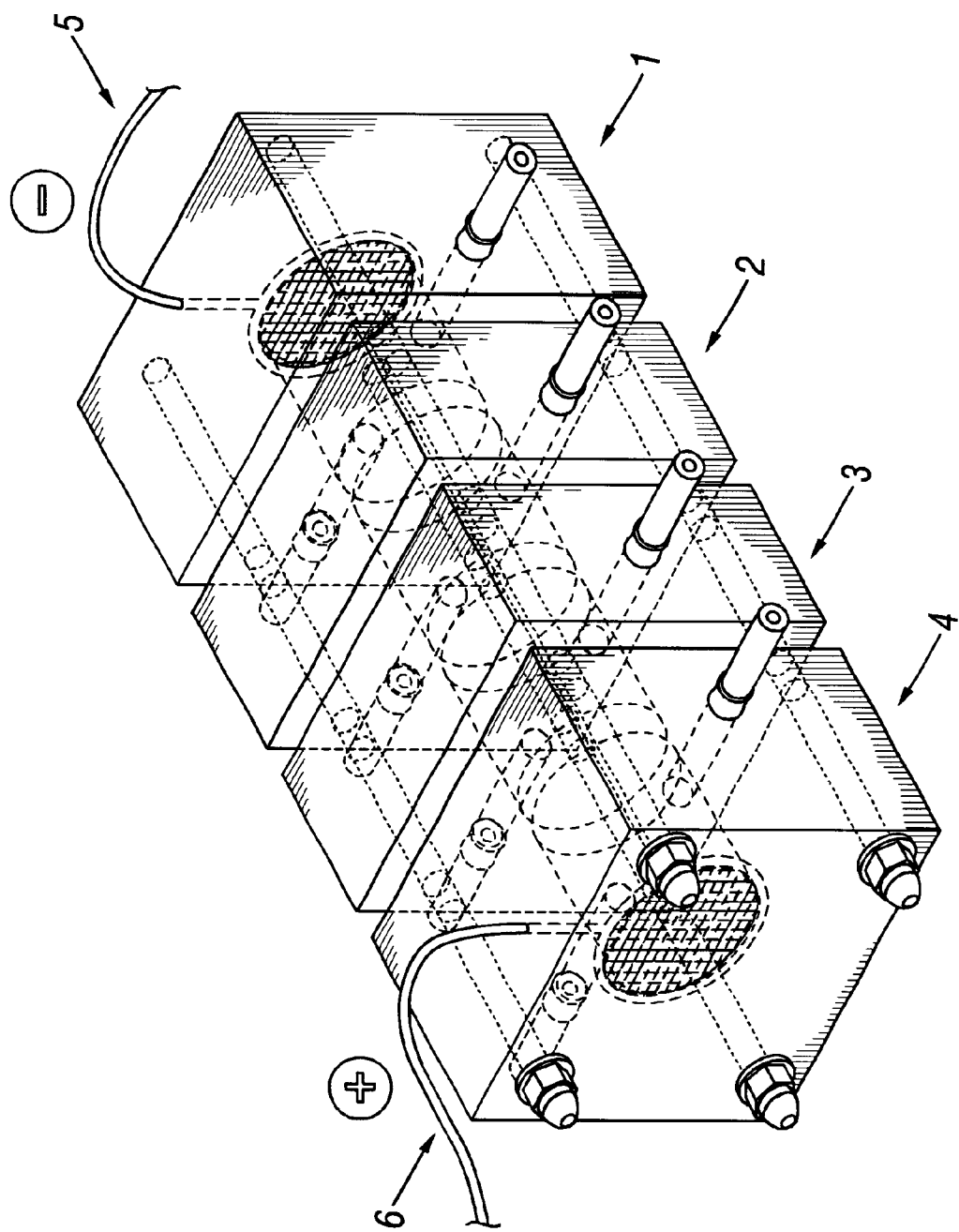

In order to shorten the distance of the electrodes and the length of the chamber, a prototype of an improved electrofiltration apparatus was designed and reduced to practice (see FIGS. 4 and 5). In this prototype two electrode chambers (2, 3) as well as the starting (1) and the filtrate chamber (4) are designed as throughput chambers (with plating net electrodes (kathode (5), anode (6)). With such a device also a cooling of the puffer or the solutions is possible. The present electrofiltration apparatus consists of 4 cylindrical segments (1, 2, 3, 4) each having a separation means, an inner diameter of 20 mm and a volume of 3.14 ml per chamber. Both outer segments are closed by 10 mm walls containing a platin net electrode (5, 6) in their inner chamber for applying voltage.

What is claimed is:

1. Method for removing pathogens from biological liquids, said biological liquids containing at least one pharmaceutically active molecule, said method comprising the steps of providing a biological liquid, wherein pathogens are potentially present, in an apparatus comprising an anode and a cathode and a membrane suitable for separating said pathogens from said pharmaceutically active molecule, said separation means being positioned between said anode and said cathode, applying current between said anode and said cathode, thereby causing one of said pathogens or said pharmaceutically active molecule to pass said separation means and recovering said pharmaceutically active molecule in a form being essentially free of said pathogens.

2. Method according to claim 1, wherein said membrane is an ultrafiltration membrane.

3. Method according to claim 1, wherein said membrane is a nanofiltration membrane.

4. Method according to claim 1, wherein said pharmaceutically active molecule is a protein.

5. Method according to claim 4, wherein said protein is a blood protein.

6. Method according to claim 4, wherein said protein is smaller than said pathogen and said membrane allows passing of said protein, but prevents passing of said pathogen.

7. Method according to claim 1, wherein said membrane is a series of membrane filters with different separation characteristics.

8. Method according to claim 7, wherein said different filtration characteristics are caused by different cut-off values of the membrane filters.

9. Method according to claim 8, wherein said cut-off values are selected to allow a separation between said pharmaceutically active molecule and aggregates of said molecule.

10. Method according to claim 1, wherein said pathogens are selected from the group consisting of hepatitis viruses, HI viruses, Parvoviruses, TT-Viruses and prion pathogens.

11. Method according to claim 1, wherein said pathogens are selected from the group consisting of HAV, HBV, HCV, HIV-1, HIV-2, Parvovirus B19 and TSE pathogen.

12. Apparatus for removing pathogens from biological liquids, said biological liquids containing at least one pharmaceutically active molecule, said apparatus comprising a container for said biological liquid, an anode, a cathode and a membrane suitable for separating said pathogen from said pharmaceutically active molecule, said separation means being positioned between said anode and said cathode and a current supply and means for applying said current between said anode and said cathode.

13. An apparatus of claim 12 wherein said membrane is an ultrafiltration membrane.

14. An apparatus of claim 12 wherein said membrane is a nanofiltration membrane.

15. An apparatus of claim 12 wherein said membrane is a series of filters with different separation characteristics.

16. An apparatus of claim 15 wherein said different filtration characteristics are caused by different cut-off values of the membrane filters.

17. An apparatus of claim 16 wherein said cut-off values are selected to allow a separation between said pharmaceutically active molecule and aggregates of said molecule.

18. Method for removing pathogens from biological liquids, said biological liquids containing at least one pharmaceutically active molecule, said method comprising the steps of providing a biological liquid, wherein pathogens are potentially present, in an apparatus comprising an anode and a cathode and a membrane suitable for separating said pathogens from said pharmaceutically active molecule, said separation means being positioned between said anode and said cathode, applying current between said anode and said cathode, thereby causing one of said pathogens or said pharmaceutically active molecule to pass said separation means and recovering said pharmaceutically active molecule in a form being essentially free of said pathogens and wherein said biological liquid is subjected to at least one virus inactivation step in said apparatus.

19. A method according to claim 18 wherein said virus inactivation step is carried out before said current is applied.

20. A method according to claim 18 wherein said virus inactivation step is selected from the group consisting of solvent/detergent treatment, detergent treatment, heating, pH lowering and chemical treatment.

* * * * *